United States Patent [19]

Pollock et al.

[11] Patent Number: 5,270,032

[45] Date of Patent: Dec. 14, 1993

[54] COMPOSITION AND METHOD FOR THE PREVENTION AND TREATMENT OF CANDIDIASIS

[75] Inventors: Jerry P. Pollock, Nesconset; Robert Renner, Kings Park; Ralph P. Santarpia, III, Jericho, all of N.Y.

[73] Assignee: The Research Foundation of State University of New York, Albany, N.Y.

[21] Appl. No.: 925,902

[22] Filed: Aug. 6, 1992

Related U.S. Application Data

[63] Continuation of Ser. No. 671,457, Mar. 19, 1991, abandoned, which is a continuation-in-part of Ser. No. 592,552, Oct. 4, 1990, abandoned.

[51] Int. Cl.$^5$ .......................... A61K 7/16; A61K 9/06
[52] U.S. Cl. ....................... 424/49; 424/52; 424/78.05; 424/663; 424/673; 514/900; 514/902; 514/967; 514/969
[58] Field of Search ................ 424/440, 443, 52, 673, 424/663; 514/900, 967

[56] References Cited

U.S. PATENT DOCUMENTS

| | | | |
|---|---|---|---|
| 2,968,597 | 1/1961 | Pagano et al. | 435/34 |
| 3,345,270 | 10/1967 | Gray | 435/34 |
| 4,030,980 | 6/1977 | Beckford et al. | 435/296 |
| 4,032,663 | 6/1977 | Kobayashi | 426/51 |
| 4,062,966 | 12/1977 | Gymer | 514/397 |
| 4,144,133 | 3/1979 | Dorn et al. | 435/254 |
| 4,454,110 | 6/1984 | Cáslavsk et al. | 424/54 |
| 4,569,837 | 2/1986 | Suzuki et al. | 514/772.2 |
| 4,661,493 | 4/1987 | Gibbs | 514/252 |
| 4,725,576 | 2/1988 | Pollock | 424/520 |
| 4,861,582 | 8/1989 | Pollock | 424/520 |
| 4,892,736 | 1/1990 | Goodson | 424/443 |
| 4,950,479 | 8/1990 | Hill | 424/49 |
| 4,981,693 | 1/1991 | Higashi | 424/443 |

OTHER PUBLICATIONS

Stenderup, *Acta Dermatology Veneraeol* [Stockholm], 121, 27-37 (1986).

Dreizen, *The American Journal of Medicine*, 28-33 (1984).

Klein et al., *New England Journal of Medicine*, 311, 354-358 (1984).

Budtz-Jörgensen, *Scand. J. Dent. Res.*, 82, 151-190 (1974).

DePaola et al., *Clinical Preventive Dentistry*, 8 (5), 3-8 (1986).

Fardal et al., *Journal American Dental Association*, 112, 863-869 (1986).

Olsen, *Acta Odont. Scand.*, 32, 329-333 (1974).

Lee et al., "An Amino Acid Liquid Synthetic Medium for the Development of Mycelial and Yeast Forms of *Candida albicans*", Sabouraudia, 13, 148-153 (1975).

Budtz-Jörgensen et al., *Acta Odontol. Scand.*, 36, 83-87 (1977).

Olsen, *Acta Odont. Scand.*, 33, 47-52 (1975).

(List continued on next page.)

Primary Examiner—Thurman K. Page
Assistant Examiner—Raj Bawa
Attorney, Agent, or Firm—Hoffmann & Baron

[57] ABSTRACT

A method for treating Candida infections of surfaces and cavities of dentures, the oral and vaginal cavities is disclosed. The method includes contacting an antifungal formulation onto the surface or cavity which is infected with the Candida fungus. The antifungal formulation includes a humectant in a concentration from about 20% to about 80%, lytic activating agents including inorganic monovalent anions and detergents. The antifungal formulation is contacted to the infected surface or cavity by suitable carrier or dispenser. The method is preferably directed towards the treatment of denture stomatitis in the oral cavity. The method preferably includes forming a replica of the denture surface using a suitable fungal growth medium to determine the location and, then, contacting the infected denture surface and surface of the oral cavity with the antifungal formulation.

19 Claims, 4 Drawing Sheets

OTHER PUBLICATIONS

Bergendal et al., *Scand J. Dent. Res.*, 88, 446–454 (1980).
Scher et al., *The Journal of Prosthetic Dentistry*, 40, 622–627 (1978).
Budtz-Jörgensen, *Acta Odontolog. Scand.*, 28, 71–90 (1970).
Budtz-Jörgensen, *JADA*, 96, 474–479 (1978).
Tarbet, *The Journal of Prosthetic Dentistry*, 48, 647–652 (1982).
Davenport, *Brit. Dent. J.*, 129, 151–156 (1970).
Merck & Co., Inc., *The Merck Index*, p. 293, 2057, "Chlorhexidine", (10th edition, 1983).
Santarpia et al., *The Journal of Prosthetic Dentistry*, 63 (4), 437–443 (1990).
Santarpia et al., *The Journal of Prosthetic Dentistry*, 60 (1), 62–70 (1988).

○ CONTROL CULTURE GROWTH.
△ CULTURE GROWTH WITH 0.1% SODIUM DODECYL (LAUROYL) SULFATE.
▲ CULTURE GROWTH WITH 0.5% SODIUM DODECYL SULFATE.
□ CULTURE GROWTH WITH 0.1% SODIUM LAUROYL SARCOSINATE.
■ CULTURE GROWTH WITH 0.5% SODIUM LAUROYL SARCOSINATE.

5,270,032

COMPOSITION AND METHOD FOR THE PREVENTION AND TREATMENT OF CANDIDIASIS

CROSS-REFERENCE TO RELATED APPLICATION

This is a file wrapper continuation or U.S. application Ser. No. 671,457 filed on Mar. 19, 1991, now abandoned which is continuation-in-part of U.S. application Ser. No. 592,552 filed on Oct. 4, 1990 now abandoned.

BACKGROUND OF THE INVENTION

The present invention relates to compositions and methods for the prevention and treatment of candidiasis.

Candidiasis is a common infectious disease of both the oral and vaginal cavities. The disease is caused primarily by *Candida albicans*, but other Candida species may also be involved.

Yeast infections are called opportunistic because the yeasts exploit a situation that is opportune for them, namely, weakness of the host, see, Stenderup, *Acta Dermatology Veneraeol [Stockholm]*, 21, 27-37 (Supplement 1986). In the human mouth, albicans is a normal microbial inhabitant found at low levels in comparison to the indigenous bacterial flora. However, of the multitude of microorganisms that frequent the oral cavity, it is this yeast species, rather than the bacterial population, which is most likely to turn pathogen when conditions are propitious; see, e.g. Dreizen, *American Journal of Medicine*, Oct. 30, 28-33 (1984). The same is true for the vaginal cavity, where Candida causing vaginitis is one of the most common gynecological problems seen in women of all ages. Although scientists have successfully solved many mysteries of complex human pathology, vaginal infections still remain annoying, distressing and persistent infections for many patients.

Oral candidiasis is seen frequently in two populations, patients wearing dentures and patients who are immunosuppressed or have AIDS. In the case of the AIDS patients, the oral Candida invasion is usually severe and is one of the earliest signs of human immune deficiency virus infection, occurring prior to the development of opportunistic infections and full blown AIDS; as discussed by Klein et al., *New England Journal of Medicine*, 311, 354-358 (1984). Presently, there is no known explanation for this localized oral candidiasis, nor is it known whether the oral candidiasis itself plays a role in the development of systemic infections. Because of the severity of infection on the mucosal surface in AIDS patients, antifungal agents are usually prescribed at high dose levels. Such high dosage of antifungals are undesirable since the currently available prescription antifungals have toxic side effects. In addition, treatment failure is often observed.

In the case of the denture stomatitis patients and also in the vaginitis patients, one of the major problems in treating with prescription antifungals is that the disease recurs soon after treatment with a commercial antifungal is terminated. Investigators have found that this recurrence is due to an inability to destroy *C. albicans* which adheres to and grows on the acrylic resin surface of the denture; see, Budtz-Jorgensen, *Scandinavian Journal Dental Research*, 82, 151-190 (1974). Therefore, the denture simply reinfects the maxillary palatal mucosal surface to initiate, maintain and continually aggravate the patient's oral candidiasis infection. Current antifungal therapy of denture stomatitis requires treatment of both the denture and the palatal mucosa. Despite the recurrence of infection, some success has been achieved with the use of prescription antifungals such as chlorhexidine and nystatin as well as with the nonprescription mouthrinse, Listerine, as reported by DePaola et. al, *Clinical Preventive Dentistry* 5, 3-8 (1986); and Fardal et al., *Journal American Dental Association*, 112, 863-869 (1986).

A method to directly test for yeasts and fungi on the surface on dentures is described by Olsen, "Denture Stomatitis Occurrence and Distribution of Fungi", *Acta. Odont. Scand.*, 32, 329-333 (1974). At page 330 Olsen discloses the use of a modified sabouraud dextrose agar, which includes penicillin and streptomycin to suppress bacterial growth. The agar is poured into the fitting surface of an upper denture after the denture was boxed in wax. The agar was allowed to set for about an hour at 4° C. and incubated for 72 hours at 37° C. A palatal model was also taken with Coe alginate, rimmed with wax and tested with the same agar, as described above. Nine different yeast species were identified including five species of Candida including *Candida albicans*, three species of Torulopsis, and one species of Kluyveromyces. We note that Olsen utilized a general yeast/fungi medium not specifically selective for Candida.

A Candida selective synthetic medium is disclosed by Lee. et al. in "An Amino Acid Liquid Synthetic Medium for the Development of Mycelial and Yeast Forms of *Candida albicans*", *Sabouraudia*, 13, 148-153 (1975).

Various other media and apparatus for the detection of yeasts, and fungi, specifically for the detection and growth of *Candida albicans* are also disclosed in the patent literature. For example, U.S. Pat. No. 4,144,133 to Dorn, et al. discloses a fungal growth media which is made of a mixture of oxgall, purified saponin, a substrate for phenol oxidase and a supporting agent, such as agar to facilitate rapid identification of a variety of pathogenic fungi which may be obtained from a sample of body fluid. The growth media provides rapid differential identification of *Candida albicans* and *Cryptococcus neoformans*.

U.S. Pat. No. 4,030,980 to Beckford, et al. discloses an apparatus for identifying a number of the most frequently isolated medical yeasts employing a single tube in a multi-cavity plate. The tube contains a sterile, liquid media to test for germ-tube production. The plate is divided into eleven independently sealed peripheral wells containing sterile solid media for the performance of urea, carbohydrate and nitrate tests. A central, optically-transparent well contains corn-meal agar for the morphological examination of yeasts, including *Candida albicans*. Also, U.S. Pat. No. 3,345,270 to Gray discloses a diagnostic composition for the rapid and positive identification of various yeast species, including *Candida albicans*, by coloration of the medium. The medium includes agar, sucrose and proteose peptone, as well as an antibacterial agent such as neomycin, penicillin or streptomycin.

Also, U.S. Pat. No. 2,968,597 discloses a diagnostic culture medium for the detection of *Candida albicans*. The medium contains a source of carbon and energy, such as nitrogen, a broad spectrum antibacterial antibiotic and a monotetrazolium indicator. When *Candida albicans* cultures are incubated on the medium, a pink or violet color develops on the medium.

Various patent and non-patent publications describe anti-fungal agents for oral use to treat *Candida albicans*. For example, U.S. Pat. No. 4,725,576 to Pollock, et al. describes polypeptides containing a substantial portion of L-histidine as effective oral fungicidal agents. The patent describes a denture adhesive paste, powder, mouth spray and mouth wash formulation containing the anti-fungal composition. The composition is especially effective against *Candida albicans*.

Also, U.S. Pat. No. 4,062,966 to Gymer is directed to 1-aryl-2-(1-imidazolyl) alkyl ethers and thioethers having antifungal properties. Gymer discloses that the compounds of the invention in the pharmaceutically acceptable acid addition salts are useful for combatting fungal infections in humans. Use in combatting infections caused by *Candida albicans* and the administration of these compounds orally and topically is also disclosed.

Various other patent and non-patent publications discussing oral and vaginal fungal infections, and anti-fungal agents include: U.S. Pat. No. 4,661,493 entitled "Tioconazole and Related Compounds for Control of Herpes Simplex Virus"; Budtz-Jorgensen, et al., "Chlorhexidine gel and Steradent ® employed in cleaning dentures", *Acta Odontol. Scand.*, 36, 83-87 (1977); Bergendal, et al., "Effect of nystatin in the treatment of denture stomatitis", *Scand. J. Dent Res.*, 88, 446-454 (1980); Scher, et al., "Antimycotic denture adhesive in treatment of denture stomatitis, The Journal of Prosthetic Dentistry", 40, 622 (1978); Butz-Jorgensen, et al., "Denture Stomatitis, The Etiology in Relation to Trauma and Infection", *Acta Odontolog. Scand.*, 28, 71-90 (1970); Butz-Jorgensen, "Clinical aspects of Candida infection in denture wearers", *JADA*, 96, 474-479 (1978); Tarbet, "Denture plaque: Quiet destroyer", *The Journal of Prosthetic Dentistry*, 48, 647 (1982); Davenport, "The Oral Distribution of Candida in Denture Stomatitis", *Brit Dent. J.*, 129, 151-156 (1970); *The Merck Index*. An Encyclopedia of Chemicals, Drugs and Biologicals, p. 293, 2057, "chlorhexidine", (10 edition 1983).

In view of the foregoing discussion, a prudent approach to the elimination of oral candidiasis would be a preventive approach, rather than a treatment approach which either fails because of severity of the disease or fails because of the need to terminate the use of the prescription antifungals. In terms of the severity of the disease, treatment is often complicated because yeasts ar normally present within a bacterial matrix or plaque. Often the infection is exacerbated by the intricate weaving of molecular interactions of *C. albicans* within the edifice of other plaque microorganisms. The latter acts as a protective fortress for the Candida pathogen by preventing the attack, not only from newly synthesized and large quantities of host defense proteins responding to the yeast challenge, but also from prescribed commercially available antifungal formulations.

Ideally, therefore, it would be a desirable goal to utilize antifungals that are fungilytic and bacteriolytic (lyse bacterial cells). In this manner, the network of bacteria and fungi that resides on the oral (and likely vaginal) surfaces and the acrylic denture surface will be disrupted and shed allowing the deeper layers of the plaque which contain hidden yeast to now become accessible to the antifungal agent.

SUMMARY OF THE INVENTION

These and other goals are accomplished by the present invention which describes compositions applied topically and adapted for prevention and treatment of candidiasis and denture stomatitis caused by *Candida albicans* and other Candida and fungal species. Primarily, the use of these compositions is for application to the oral and vaginal cavities. We propose, however, that these compositions would also be of use in other locales of an organism, as well as in the treatment of surfaces and instruments that may come in contact within an animal or human body. The compositions include the lytic facilitators sorbitol and glycerol or comparable type humectant compounds at concentrations of about 20% to 80%, preferably from about 30% to 80% weight/volume. Although not fungilytic by themselves, these humectants will cause lysis of Candida cells in the presence of lytic activators such as inorganic monovalent anions, nonionic detergents and anionic detergents. This lysis is accompanied by fungicidal death, particularly with the active fungicidal agent, sodium lauroyl sarcosinate, or other anionic detergents used at 0.01% to 1% concentration. The compositions further comprise bicarbonate ion at 0.5% to 2% and if desired thiocyanate, chloride or fluoride ion at 0.5% to 2%; and also Tween 20 or other nonionic detergents or similar compounds at 0.01% to 3%. In addition, alcohol may be included to a level of 15% along with appropriate sweetening and flavoring agents. The final compositions also have proven bacteriolytic properties. Other formulation ingredients and water are then added to 100 percent.

The compositions are administered in a manner and vehicle suitable for oral or vaginal cavity administration. The invention also relates to using such compositions for preventing and treating oral candidiasis and denture stomatitis which is a type of oral candidiasis. The compositions of the present invention are conventionally formulated into mouthrinses, mouthsprays, toothpastes, denture cleansers and denture-care products and vaginal creams and vaginal-care products. While it has been found effective to kill and lyse *C. albicans* in the sites of the oral cavity, the invention is not limited to the destruction of this yeast species or other Candida species in that location. Rather, the composition can be administered to any species or object that is brought in contact with the species to kill and lyse the yeast on the treated object or species.

The present invention further includes a one-step in vivo method for detection of *C. albicans* on the surface of a denture of denture stomatitis (DS) patients. This one step method includes removing a denture from a patient's mouth coating the edges of the denture with a wax or wax-like substance, introducing a Candida selective media, such as that disclosed by Lee et al., *Sabouraudia*, 13, 148-153 (1975), supplemented with arginine, zinc sulphate and 2% agar, onto the surface of the denture. After the agar hardens, the model is removed from the denture and incubated at room temperature for a period of one to four days. Colonies of *Candida albicans* corresponding to the location of infection of both denture and palate of the patient can be observed on the model. Accordingly, the present invention also includes using the antifungal wash, soak, rinse or toothpaste of the present invention to treat the oral cavity in locations in the denture on which the colonies of the *Candida albicans* are detected on the model. The antifungal formulation of the present invention can be used repeatedly with the one step in vivo detection method until all colonies of *Candida albicans* have been eliminated.

For a better understanding of the present invention, references made to the following description and examples taken in conjunction with the accompanying tables and figures, the scope of which is pointed out in the appended claims.

DETAILED DESCRIPTION OF THE INVENTION

Figure 1:
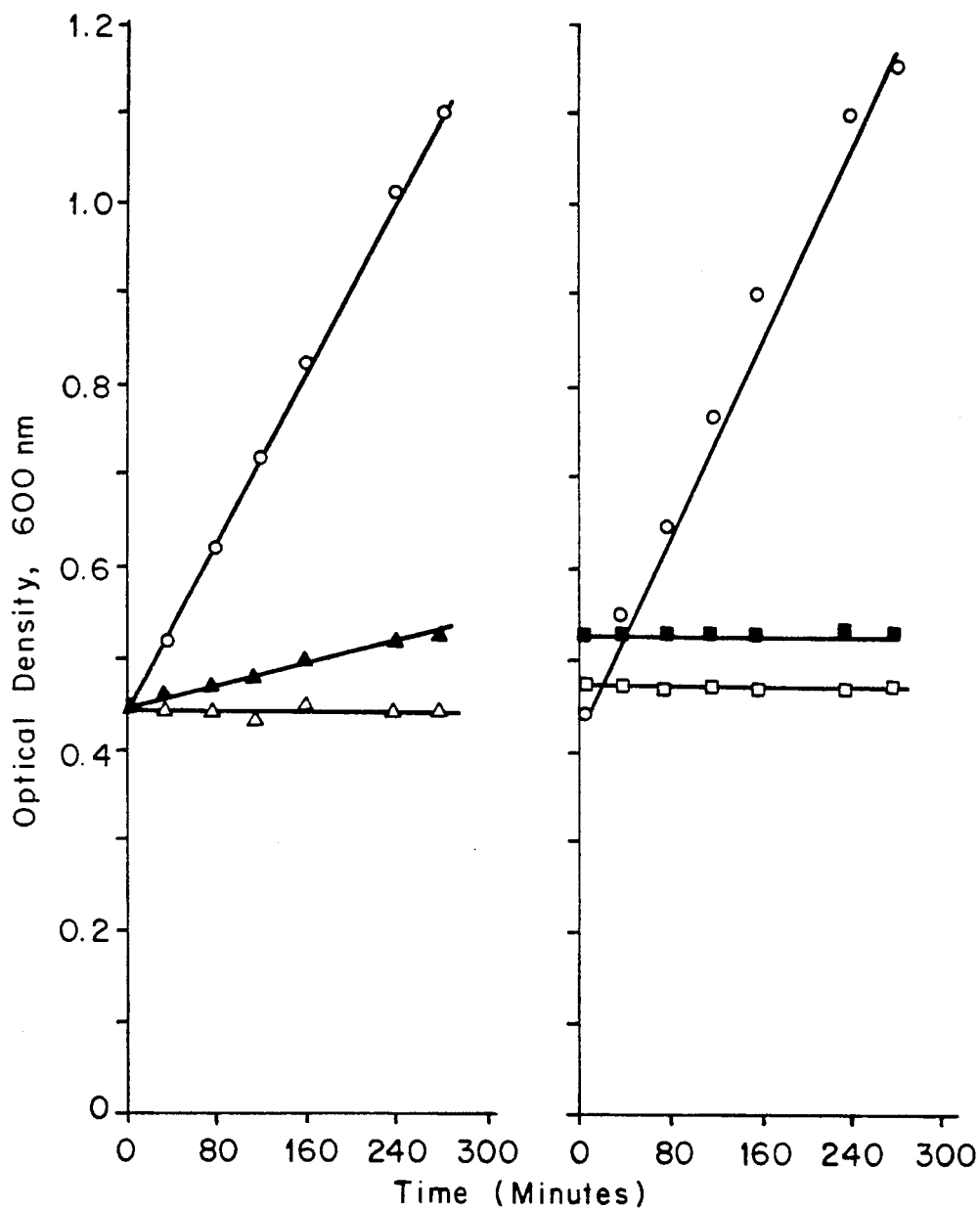
FIG. 1 shows graphs comparing the effect of anionic surfactants on the growth of *Candida albicans* GDH 2023.

The present invention relates to compositions applied topically and adapted for prevention and treatment of candidiasis and denture stomatitis caused by *Candida albicans* and other Candida species. Primarily, the use of these compositions is for application to the oral and vaginal cavities. We propose, however, that these compositions would also be of use in other locales of an organism, as well as in the treatment of surfaces and instruments that come in contact with an organism, including the human body. The compositions include the lytic facilitators sorbitol and glycerol or comparable type humectant compounds at concentrations of about 20% to 80%, preferably from about 30% to 80% weight/volume. Although not fungilytic by themselves, these humectants will cause lysis of Candida cells in the presence of lytic activators such as inorganic monovalent anions, nonionic detergents and anionic detergents. This lysis is accompanied by fungicidal death, particularly with the active fungicidal agent, sodium lauroyl sarcosinate, or other anionic detergents used at 0.01% to 1% concentration. The compositions further comprise bicarbonate ion at 0.5% to 2% and if desired thiocyanate, chloride or fluoride ion at 0.5% to 2%; and also Tween 20 or other nonionic detergents or similar compounds at 0.01% to 3%. In addition, alcohol may be included to a level of 15% along with appropriate sweetening and flavoring agents. The final compositions also have proven bacteriolytic properties. Other formulation ingredients and water are then added to 100 percent.

The compositions of the present invention are also bacteriolytic in nature, as described in co-pending parent application Ser. No. 592,552 U.S. Pat. No. 5,185,153, the disclosure of which is incorporated by reference herein. Not only are these compositions safe, simple to make and use, they are also powerful antifungals in treating human clinical disease. In order to test the antifungals of the present invention, we recently developed an in vivo replica technique, see, also Santarpia et al., *Journal Prosthetic Dentistry*, 63, 437–443 (1990) which localizes this yeast species in a site-specific manner on the denture surface. Patients were given our formulation as a mouthrinse and a denture soak and we observed that we could eliminate *C. albicans* from their denture surface as well as reduce the palatal inflammation. From both this in vivo data and our in vitro results, we conclude that the use of daily topical administration of our formulations will prevent oral candida infections from occurring. At the same time, we propose that our antifungal formulations can be used to treat existing candida infections on both oral and vaginal mucosal surfaces.

The finding that these compositions are fungilytic is surprising despite the fact that these same compositions are bacteriolytic. Bacterial cell walls and cell membranes are distinctly different from fungal cell walls and membranes. Since destruction of walls and membranes leads to cell lysis, the mechanisms of cell lysis are probably different in bacteria and fungi. Sorbitol, however, may cause similar swelling in both fungi and bacteria between the cell wall and membrane, accounting for its humectant lytic facilitator role. The swelling process presumably allows facilitated penetration by lytic activators.

The compositions are administered in a manner and vehicle suitable for oral or vaginal cavity administration. The invention also relates to using such compositions for preventing and treating fungal infection on the surface or interior of an organism, or other surfaces that come in contact with an organism. The present invention is especially useful for preventing and treating oral candidiasis and denture stomatitis, which is a type of oral candidiasis. The compositions of the present invention are conventionally formulated into mouthrinses, mouthsprays, toothpastes, denture cleansers and denture-care products and vaginal creams and vaginal-care products. While it has been found effective to kill and lyse *C. albicans* in the sites of the oral cavity, the invention is not limited to the destruction of this yeast species or other Candida species in that location. Rather, the composition can be administered to any organism or object that is brought in contact with the organism to kill and lyse the yeast on the treated organism or object.

The properties of the compositions of the present invention are determined both by standardized in vitro assay procedures and also by in vivo human clinical studies. Cell death is measured by the number of surviving yeast colony forming units compared to untreated controls plated onto appropriate mycological agar media. Spectrophotometric reductions in turbidity accompanied by cell death are used as indications of yeast cell lysis. In vivo determinations are performed by monitoring the efficacy of our compositions in significantly reducing or eliminating *C. albicans* from the acrylic resin surface of the maxillary dentures of denture stomatitis patients, and by actual reductions in clinical palatal inflammation of these patients.

The present invention further includes a one-step in vivo method for the detection of *C. albicans* on the denture surface of a denture stomatitis (DS) patient. This one step method is generally described by Olson, "Denture Stomatitis Occurrence and Distribution of Fungi", *Acta. Odont. Seand.*, 32, 329-333 (1974). The method includes removing=denture from a patient's mouth, coating the edges of the denture with a wax or wax-like substance, introducing a Candida selective media, such as that disclosed by Lee et al., *Sabouraudia*, 13, 148-153 (1975) supplemented with arginine, zinc sulphate and 2% agar onto the surface of the denture. After the agar hardens, the model is removed from the denture and incubated at room temperature for a period of one to four days. Colonies of *Candida albicans* corresponding to the location of infection of both the denture and palate of the patient can be observed on the model. Accordingly, the present invention also includes using the antifungal wash, soak, rinse or toothpaste of the present invention to treat both the denture and the oral cavity in locations corresponding to points or regions of the denture on which the colonies of the *Candida albicans* are detected on the model. The antifungal formulation of the present invention can be used repeatedly with the one-step in vivo detection method until all colonies of *Candida albicans* have been eliminated.

EXAMPLES

I. In Vitro Studies

A. Materials and Methods

Yeast Cultures

*Candida albicans* and other Candida species used in these studies were isolated from lesion sites in denture stomatitis and vaginitis patients.

Growth Experiments

In growth experiments, yeast species were grown from lyophilized cultures in potato dextrose broth to the late log phase of growth. After transfer to fresh broth, growth was allowed to proceed until mid-log phase at which point sterile solutions of the anionic detergents, sodium lauryl sulfate or sodium lauroyl sarcosinate, were added. Further growth of controls and treated samples were then monitored. After approximately two and half hours of incubation with the detergents, aliquots were withdrawn, serial diluted and then plated onto potato dextrose agar for cell viability determinations (see details of method below).

Non-Growth Experiments

In non-growth experiments, yeast cells were allowed to multiply to the mid-late log phase of growth and then were harvested and washed. Cells were then distributed and suspended in either distilled water (Control), sodium lauroyl sarcosinate, or various mouthrinse formulations of the present invention. Upon resuspension, optical densities (turbidities) at 600 nm were immediately measured and then followed over time during incubation at room temperature. In the first minute and at time points thereafter, aliquots of 100 ul of Controls, sodium lauroyl sarcosinate or the various mouthrinses were removed and diluted into 900 ul of potato dextrose broth ($10^{-1}$ dilution). Serial dilutions were then made through $10^{-6}$ and from each dilution, 100 ul was removed and plated onto potato dextrose agar. Agar plates were allowed to incubate for 48 hours at room temperature and yeast colonies were counted. Each mouthrinse was compared for its effects on yeast turbidities and viabilities (colony forming units) to control treatment of yeast pellets suspended in distilled water.

EXAMPLE 1

FIG. 1 shows the graphs which demonstrate that both anionic detergents, sodium lauroyl sulfate and sodium lauryl sarcosinate, interrupt and virtually block growth of *Candida albicans* GDH 2023, an isolate from a denture stomatitis patient. Similar effects were also seen with the vaginitis isolate, *C. albicans* GRI 2773 (data not shown).

TABLE 1

Inhibition of *Candida albicans* GDH 2023 Viability by Anionic Detergents.

| Culture | Colony forming units per ml* | Percent Inhibition** |
|---|---|---|
| Control | $1.0 \times 10^7$ | — |
| +0.1% SDS | $1.0 \times 10^6$ | 90 |
| +0.5% SDS | $1.0 \times 10^3$ | >99.9 |
| +0.1% SLS# | $5 \times 10^4$ | 99.5 |
| +0.5% SLS | -0- | 100 |

*Colony forming units were determined by removing aliquots for plating 160 minutes after addition of anionic detergents (see FIG. 1).
** Compared to the Control.
Sodium dodecyl (lauryl) sulfate abbreviated as SDS.
Sodium lauroyl sarcosinate abbreviated as SLS.

Table 1 shows that the surprising cessation of growth seen in FIG. 1 is accompanied by drastic reductions in cell viability indicating that these anionic detergents are candidacidal when yeast cells are exposed to these detergents for long periods of time ($2\frac{1}{2}$ hours, Table 1). From the observed data (Table 1), sodium lauryl sarcosinate seems to be more potent in killing *C. albicans* than sodium lauroyl sulfate. In a separate study (data not shown), sodium lauroyl sarcosinate inhibited the growth of *C. albicans* GDH 2023 even at levels of 0.01 percent.

EXAMPLE 2

Table 2 shows a comparison of various combinations of ingredients for their ability to kill *C. albicans*. In the parent application, Ser. No. 592,552, it was observed that high concentrations (usually 30% or greater) of glycerol or sorbitol (termed humectants in pharmaceutical formulations) act as bacterial lytic facilitators and promote cell lysis when used in combination with inorganic monovalent anions (for example, sodium bicarbonate and sodium thiocyanate), nonionic surfactants (for example, Tween 20) and anionic surfactants (for example, sodium lauryl sulfate and sodium lauroyl sarcosinate). However, neither the humectant alone nor each of the three activators (inorganic monovalent anions, nonionic detergents, anionic detergents) by themselves were demonstrated to cause bacteriolysis.

TABLE 2

Inhibition of *Candida albicans* GDH 2023 Viability by Mouthrinse Formulations.

| | Colony Forming Units/ml | |
|---|---|---|
| Mouthrinse | 1 min | 24 hrs |
| Water Control | $280 \times 10^4$ (—)* | $340 \times 10^4$ (—) |
| 30% Sorbitol + 1.5% Bicarbonate + 0.5% Thiocyanate | $245 \times 10^4$ (13) | $300 \times 10^4$ (12) |
| 30% Sorbitol + 1.5% Bicarbonate + 0.5% Thiocyanate + 7% Alcohol | $235 \times 10^4$ (16) | $250 \times 10^4$ (24) |
| 30% Sorbitol + 1.5% Bicarbonate + 0.5% Thiocyanate + 7% Alcohol + 1% Tween 20 | $250 \times 10^4$ (11) | $3 \times 10^4$ (99.1) |
| 30% Sorbitol + 1.5% | 0 (100) | 0 (100) |

TABLE 2-continued

Inhibition of *Candida albicans* GDH 2023 Viability by Mouthrinse Formulations.

| Mouthrinse | Colony Forming Units/ml | |
|---|---|---|
| | 1 min | 24 hrs |
| Bicarbonate + 0.5% Thiocyanate + 7% Alcohol + 1% Tween 20 + 0.5% Sodium Lauroyl Sarcosinate | | |
| 0.5% Sodium Lauroyl Sarcosinate | 4 × 10$^4$ (98.6) | 2 × 10$^4$ (99.4) |

*Values in parentheses indicate percent inhibition of viability compared to the control.

The results displayed in Table 2 show that sodium lauroyl sarcosinate is a potent antifungal, almost completely killing the population of *C. albicans*. However, as stated above, this agent alone will not effect bacteriolysis and therefore would not be useful for treating candidiasis in the in vivo situation. As discussed in the Background section, a weaving of *C. albicans* within the bacterial plaque matrix on mucosal and denture surfaces necessitates formulations which disrupt the plaque matrix so that active antifungal agents can then penetrate and attack more deeply buried viable yeast organisms. In this regard, the mouthrinse formulation of the present invention containing sorbitol, sodium bicarbonate, sodium thiocyanate, alcohol, Tween 20 and sodium lauroyl sarcosinate would seem to be ideal. First, we have shown that this formulation exhibits potent bacteriolytic capacity; and second, we now observe it to be a potent antifungal, completely killing *C. albicans* within one minute (Table 2). The formulation also effectively kills *Candida tropicalis* and *Candida glabrata* (data now shown). An unexpected finding of these studies was that even in mouthrinse formulations devoid of sodium lauryl sarcosinate, yeast killing activity was noted, albeit slower. Note, however, that the complete mouthrinse was much more effective than sodium lauryl sarcosinate alone (Table 2), suggesting a synergistic effect of sodium lauryl sarcosinate and other antifungal ingredients in the mouthrinse.

EXAMPLE 3

An additional finding of the in vitro experiments was that within the first minute of incubation of *C. albicans* with sorbitol or sorbitol mouthrinses there was a significant reduction of turbidity of the yeast cells. Table 3 shows that this reduction was dependent upon the concentration of sorbitol, which increased with increasing sorbitol concentrations.

TABLE 3

Effect of Sorbitol Concentration on Turbidity of *Candida albicans*.

| Agent | Optical Density at 600 nm | Percent Reduction in Turbidity* |
|---|---|---|
| Control Water | .93 | — |
| 20% Sorbitol | .74 | 20.4 |
| 20% Sorbitol Mouthrinse** | .76 | 18.3 |
| 30% Sorbitol | .65 | 30.1 |
| 30% Sorbitol Mouthrinse | .68 | 26.9 |
| 40% Sorbitol | .60 | 35.5 |
| 40% Sorbitol | .64 | 31.2 |

TABLE 3-continued

Effect of Sorbitol Concentration on Turbidity of *Candida albicans*.

| Agent | Optical Density at 600 nm | Percent Reduction in Turbidity* |
|---|---|---|
| Mouthrinse | | |

*Compared to the water control 1 minute after mixing *C. albicans* with agent.
**Mouthrinses contain sorbitol + 0.5% sodium lauroyl sarcosinate + 1% Tween 20 + 1.5% NaHCO$_3$ + 0.5% NaSCN + 7% alcohol.

Sodium lauroyl sarcosinate alone was not observed to rapidly decrease the turbidity of yeast cell suspensions, suggesting that this 1 minute turbidity drop (Table 3) might be an indication of yeast cell lysis (fungilysis). In the parent application it was noted that sorbitol does not kill bacteria, but rather acts as a lytic facilitator, which when added to lytic activating agents (these agents do not promote cell lysis in the absence of sorbitol) such as inorganic monovalent anions (sodium bicarbonate and sodium thiocyanate), nonionic detergents (Tween 20) and anionic detergents (sodium lauryl sulfate or sodium lauroyl sarcosinate) promotes bacteriolysis.

EXAMPLE 4

To determine whether the turbidimetric differences noted above with the different sorbitol concentrations might play a role in yeast cell lysis and consequential cell death, we tested these agents for their effects on viability of the Candida cells.

TABLE 4

Effect of Sorbitol Concentrations on Viability of *Candida albicans*

| Agent | Colony Forming Units/ml | |
|---|---|---|
| | 1 min | 24 hrs |
| Water Control | 340 × 10$^4$ (—)* | 380 × 10$^4$ (—) |
| 20% Sorbitol | 335 × 10$^4$ (0) | 380 × 10$^4$ (0) |
| 20% Sorbitol Mouthrinse ** | 88 × 10$^4$ (74) | 0 (100) |
| 30% Sorbitol | 330 × 10$^4$ (0) | 370 × 10$^4$ (0) |
| 30% Sorbitol Mouthrinse | 0 (100) | 0 (100) |
| 40% Sorbitol | 335 × 10$^4$ (0) | 375 × 10$^4$ (0) |
| 40% Sorbitol Mouthrinse | 0 (100) | 0 (100) |

*Values in parentheses indicate percent inhibition of viability compared to the control.
**Mouthrinses contain sorbitol + 0.5% sodium lauroyl sarcosinate + 1% Tween 20 + 1.5% NaHCO$_3$ + 0.5% NaSCN + 7% alcohol.

Table 4 shows that sorbitol by itself was not lytic since it was not active in killing *C. albicans*, this is analogous to our bacterial findings. In contrast, both the 30% and 40% mouthrinses were completely effective in destroying this yeast species. Surprisingly, the 20% sorbitol mouthrinse, even with the sodium lauroyl sarcosinate, was only partially effective after one minute in killing *C. albicans*. Since the sorbitol concentration was the only difference, we conclude that the observed increased reduction in turbidity (see Table 3, compare 20% sorbitol to 30% and 40% sorbitol) is the limiting factor in the killing activity observed in the death of the *C. albicans*. Accordingly, analogous to bacteria, we suggest that the sorbitol acts as a lytic facilitator (it itself does not lyse the cells) even though slightly greater optical density decreases are noted for free sorbitol compared to the mouthrinses (see Table 3). Lysis and consequential cell death are only observed when lytic activating agents such as sodium lauroyl sarcosinate, Tween 20 or inorganic salts are added to the sorbitol. Furthermore, the lysis and killing are maximal only when sufficiently high concentrations of sorbitol (30% or greater) are used in the mouthrinse formulations.

IN VIVO EXAMPLES

Clinical Studies

Human clinical studies were performed with volunteer denture stomatitis patients. Prior to their being admitted into the study, patients had their palatal and denture surfaces analyzed to determine if *C. albicans* was present and thus the likely cause of their oral candidiasis; in accordance with Santarpia et al., *Journal Prosthetic Dentistry*, 60, 62–70 (1988).

EXAMPLE 5

The following preferred denture soak was formulated in accordance with the present invention:

TABLE 5

Components of the preferred dental soak formulation based on a total volume of 100 ml.

| Component | Concentration |
| --- | --- |
| Sorbitol | 30 gm |
| Tween 20 | 1.0 ml |
| Sodium Bicarbonate | 1.5 gm |
| Sodium Thiocyanate | 0.5 gm |
| Sodium Lauroyl Sarcosinate | 0.5 gm |
| Alcohol | 7.5 ml |
| Distilled water q.s. | 100 ml |

There were three patients in the initial trial which was conducted over a two-day period. On the first day, agar replicas of the patients' dentures, using an agar synthetic medium selective for *C. albicans*, were made and incubated at room temperature to permit the growth of this yeast species, in accordance with the present invention and as generally described by Santarpia et al., *Journal Prosthetic Dentistry*, 63, 437–443 (1990). Patients were then instructed to soak their dentures overnight in 100 ml of the dental soak (but not to rinse their mouths) and to return for further testing. On the following day, replicas of the maxillary denture were again poured and incubated for exactly the same time periods as untreated controls. Photographs were taken of all agar replicas during a 72-hour incubation period.

The results showed that overnight treatment with the dental soak formulation of this invention (Table 5) was capable of reducing more than half of the *C. albicans* residing on the denture surface of the three patients.

The results of the initial clinical trial (Example 5) suggested that a longer time period was needed to significantly reduce Candida growing on the denture surface. Accordingly, the next clinical trial (Example 6) was conducted over a period of a week, and a second preferred formulation (see Table 6) was given both as a denture soak and as a mouthrinse to determine if palatal mucosal inflammation could be reduced in this short time period.

EXAMPLE 6

The following preferred flavored mouthrinse and denture soak was formulated in accordance with the present invention:

TABLE 6

Components of a second preferred flavored mouthrinse and denture soak formulation, based on a total volume of 100 ml.

| Component | Concentration |
| --- | --- |
| Sorbitol | 30 gm |
| Tween 20 | 1.0 ml |
| Sodium Bicarbonate | 1.5 gm |
| Sodium Thiocyanate | 0.5 gm |
| Sodium Lauroyl Sarcosinate | 0.7 gm |
| Alcohol | 7.5 ml |
| Pluronic F127 | 0.012 gm |
| Oil of Peppermint | 0.1 ml |
| Distilled water q.s. | 100 ml |

There were five patients in the second clinical trial. The replica procedures were the same as those described in the first trial except that patients were seen initially and after one week using the rinse and denture soak. In addition, patients were instructed to rinse their mouths twice daily (morning and night) with a tablespoon of the mouthrinse. In order to compare mucosal surfaces before and after treatment, intraoral photographs were taken of the patients' maxillary palates.

Figure 2A:
FIG. 2A shows the *C. albicans* growth on agar replica of maxillary denture of patient #1.
Figure 2B:
FIG. 2B shows virtual absence of *C. albicans* colonies on denture replica of patient #1 after one week of denture soaking and twice daily mouthrinsing with the antifungal formulation of the present invention, as described in Example 6.
Figure 3A:
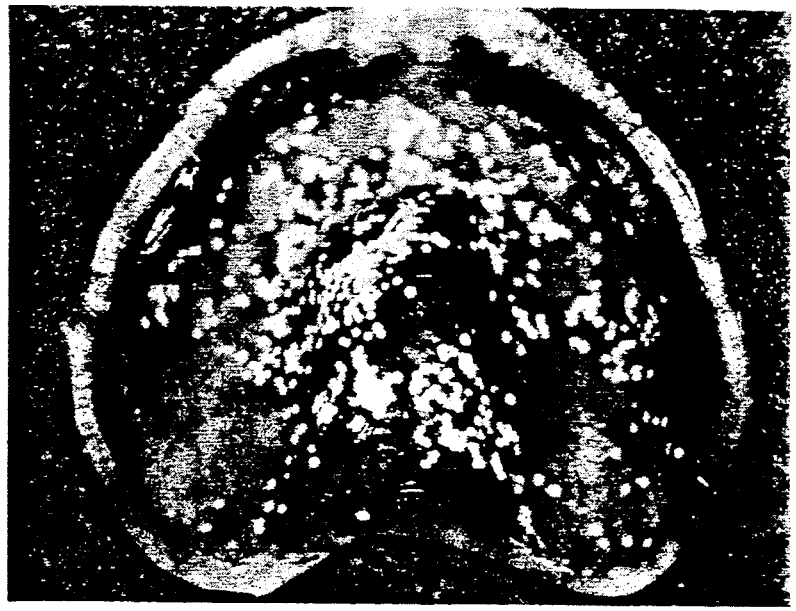
FIG. 3A shows *C. albicans* growth on agar replica of maxillary denture of patient #2.
Figure 3B:
FIG. 3B shows virtual absence of *C. albicans* on denture replica of patient #2 after one week of denture soaking and twice daily mouthrinsing with the antifungal formulation of the present invention, as described in Example 6.
Figure 4A:
FIG. 4A shows *C. albicans* growth on agar replica of maxillary denture of patient #3.
Figure 4B:
FIG. 4B shows virtual absence of *C. albicans* on denture replica of patient #3 after one week of denture soaking and twice daily mouthrinsing with the antifungal formulation of the present invention, as described in Example 6.

After one week of treatment, all five patients virtually had no *C. albicans* on their dentures despite the fact that the organism was present on some patients' dentures at very high levels prior to treatment. After this short treatment, two of the patients showed reduced mucosal inflammation while the other three were slightly improved. In longer treatment (two weeks or more) with antimicrobial rinses, we have observed that the patients' palatal inflammation further improves. FIGS. 2–4 show the reduction in *C. albicans* colonies appearing on the agar replicas after one week of denture soaking and twice daily mouthrinsing for three of the five patients in the study.

In addition to mouthrinses, the lytic, antifungal formulation of the present invention could easily be incorporated into other formulations described in Examples 7–15:

EXAMPLE 7

TABLE 7

Preferred mint flavored mouthrinse formulation in accordance with the present invention.

| Component | Concentration |
| --- | --- |
| Sorbitol | 80 gm |
| Sodium Bicarbonate | 2 gm |
| Sodium Thiocyanate | 2 gm |
| Sodium Lauroyl Sarcosinate | 1 gm |
| Tween 20 | 3 ml |
| Alcohol | 15 ml |
| Pluronic F127 | 0.012 gm |
| Oil of Peppermint | 0.1 ml |
| Water q.s. | 100 ml |

The formulation is utilized by rinsing the mouth for about 30 to 60 seconds from 1–3 times per day with about 15 ml of undiluted mouthwash.

EXAMPLE 8

TABLE 8

Preferred mouthspray formulation in accordance with the present invention.

| Component | Concentration |
| --- | --- |
| Glycerol | 40 ml |
| Sodium Bicarbonate | 1.5 gm |
| Sodium Thiocyanate | 0.5 gm |
| Sodium Lauroyl Sarcosinate | 0.5 gm |

TABLE 8-continued

Preferred mouthspray formulation in accordance with the present invention.

| Component | Concentration |
| --- | --- |
| Tween 20 | 1 ml |
| Saccharin Sodium | 0.07 gm |
| Peppermint Spirit | 15 ml |
| Water q.s. | 100 ml |

The formulation is utilized by spraying aliquots of 0.25 to 0.50 ml onto each quadrant of the gingival and tooth surface between 1 and 3 times per day.

EXAMPLE 9

TABLE 9

Preferred toothpaste gel formulation in accordance with the present invention.

| Component | Concentration |
| --- | --- |
| Glycerin | 40 ml |
| Sodium Bicarbonate | 2 gm |
| Sodium Thiocyanate | 1 gm |
| Sodium Lauroyl Sarcosinate | 1 gm |
| Tween 20 | 3 ml |
| Carboxymethyl Cellulose 120H | 1.8 gm |
| Saccharin Sodium (50% soln) | 0.2 ml |
| Oil of Peppermint | 2 ml |
| Mineral Oil | 2 ml |
| Silica | 21 gm |
| Water q.s. | 29 ml |

This formulation is utilized by cleaning the teeth with about 1 to 2 gm of paste between 1 to 3 time per day.

EXAMPLE 10

TABLE 10

Preferred denture tablet cleanser formulation in accordance with the present invention.

| Component | Concentration |
| --- | --- |
| Sorbitol | 1900 mg |
| Sodium Bicarbonate | 80 mg |
| Sodium Thiocyanate | 80 mg |
| Sodium Lauryl Sulfate | 40 mg |
| Tween 20 | 40 mg |
| Potassium Monopersulfate | 960 mg |
| Sodium Borate Perhydrate | 480 mg |
| Citric Acid | 360 mg |
| Sodium Carbonate | 32 mg |
| Magnesium Stearate | 18 mg |
| Silica | 14 mg |
| Flavor | as needed |

Dissolve each tablet in one denture cup (approximately 4 ounces) of water. Soak denture in antimicrobial denture cleanser for short periods (15 minutes) or longer periods (overnight). Rinse denture with water prior to reinsertion in the mouth.

EXAMPLE 11

TABLE 11

Preferred denture adhesive powder formulation in accordance with the present invention.

| Component | Concentration |
| --- | --- |
| Sorbitol | 30 gm |
| Sodium Bicarbonate | 1 gm |
| Sodium Thiocyanate | 1 gm |
| Sodium Lauryl Sulfate | 1 gm |
| Karaya Gum | 64.6 gm |
| Pluronic F127 | 1.9 gm |
| Calcium Silicate | 0.1 gm |

TABLE 11-continued

Preferred denture adhesive powder formulation in accordance with the present invention.

| Component | Concentration |
| --- | --- |
| Flavor* | 0.4 gm |

*Examples of flavoring constituents are flavoring oils; for example, oils of spearmint, peppermint, wintergreen, sassafras, cloves, sage eucalyptus, marjoram, cinnamon, lemon, orange, and methyl salicylate.

Apply powder to denture after overnight soaking in a denture cleanser. Rinse denture with water and sprinkle antimicrobial powder (approximately 1 to 2 gm) onto the surface of each denture and insert into the mouth.

EXAMPLE 12

TABLE 12

Preferred denture adhesive paste formulation in accordance with the present invention.

| Component | Concentration |
| --- | --- |
| Glycerol | 30 gm |
| Sodium Bicarbonate | 0.5 gm |
| Sodium Thiocyanate | 0.5 gm |
| Sodium Lauryl Sulfate | 1.0 gm |
| Pluronic F127 | 3 gm |
| Petrolatum | 35 gm |
| Liquid Petrolatum | 5 gm |
| Propyl Paraben | 0.1 gm |
| Carboxymethylcellulose Gum | 25 gm |
| Flavor | 0.05 gm |

Apply paste to denture after overnight soaking in denture cleanser. Rinse denture with water and apply a thin film of paste (approximately 2 gm) onto the surface of each denture and insert into the mouth.

EXAMPLE 13

TABLE 13

Preferred vaginal cream formulation in accordance with the present invention.

| Component | Concentration Percent (W/W) |
| --- | --- |
| Sorbitol | 30 |
| Glycerin | 10 |
| Sodium Bicarbonate | 1 |
| Sodium Thiocyanate | 1 |
| Sodium Lauroyl Sarcosinate | 0.5 |
| Tween 20 | 1 |
| Cetyl Alcohol | 0.5 |
| Stearic Acid | 25 |
| Triethanolamine | 0.2 |
| Methyl Paraben | 0.1 |
| Propyl Paraben | 0.1 |
| Water q.s. | 100% |
| pH adjusted to 5.5 | |

For topical use, gently massage cream into the affected and surrounding areas twice daily (morning and evening). For invaginal use, apply about 5 gm of cream with applicator high into the vaginal vault once or twice daily. Continue as indicated until vaginitis is eliminated (usually two to four weeks).

EXAMPLE 14

TABLE 14

Preferred vaginal suppositories formulation in accordance with the present invention.

| Component | Concentration Percent (W/W) |
| --- | --- |
| Sorbitol | 20 |
| Glycerin | 20 |
| Polyethylene Glycol 4000 | 20 |

TABLE 14-continued

Preferred vaginal suppositories formulation in accordance with the present invention.

| Component | Concentration Percent (W/W) |
| --- | --- |
| Polyethylene Glycol 1000 | 20 |
| Tween 20 | 2 |
| Sodium Bicarbonate | 2 |
| Sodium Thiocyanate | 2 |
| Sodium Lauroyl Sarcosinate | 0.5 |
| Methyl Paraben | 0.1 |
| Propyl Paraben | 0.1 |
| Water q.s. | 100% |
| pH adjusted to 5.5 | |

Insert one 3 gram suppository into the vaginal vault once to twice daily. Continue as indicated until vaginitis is eliminated (usually two to four weeks.

EXAMPLE 15

TABLE 15

Preferred vaginal deodorant solution formulation in accordance with the present invention.

| Component | Concentration Percent (W/W) |
| --- | --- |
| Sorbitol | 33 |
| Sodium Bicarbonate | 0.5 |
| Sodium Thiocyanate | 0.5 |
| Sodium Lauroyl Sarcosinate | 0.5 |
| Alcohol | 5 |
| Tween 20 | 0.5 |
| Sodium Acetate | 0.17 |
| Acetic Acid | 0.08 |
| Sodium Chloride | 1 |
| Menthol | 0.25 |
| Thymol | 0.25 |
| Methyl Salicylate | 0.5 |
| Water q.s. | 100% |
| pH adjusted to 5.5 | |

Thus, while we have described what are the presently contemplated preferred embodiments of the invention, further changes and modifications could be made by those skilled in the art without departing from the scope of the invention, and it is contemplated to claim all such changes and modifications.

We claim:

1. A method for treating Candida infections, comprising:

contacting an antifungal formulation onto a surface or cavity of a denture, an oral or vaginal cavity which is infected with Candida, the antifungal formulation consisting essentially of:

humectant in a concentration of from about 20% to about 80%; and lytic activating agents selected from the group consisting of inorganic movement anions in a concentration of 0.5% to 2% said inorganic monovalent anions is selected from the group consisting of bicarbonate, thiocyanate, chloride and fluoride ions; anionic surfactant detergent in a concentration from 0.05% to about 1%, said anionic surfactant detergent is selected from the group consisting of sodium lauroyl sarcosinate and sodium lauroyl sulfate; and non-ionic surfactant detergent in a concentration of from about 0.01% to about 3%, said non-ionic surfactant detergent is selected from the group consisting of Tween 20, polymers of polyoxyethylene and polymer of polypropylene, wherein the formulation is contacted to the infected surface or cavity of the oral cavity, denture or vagina by a suitable dispenser.

2. The method recited in claim 1, wherein said humectant is selected from the group consisting of glycerol, sorbitol, glycol, and corn syrup.

3. The method recited in claim 2 wherein said humectant is present in the concentration of from about 30% to about 50%.

4. The method recited in claim 1 wherein said humectant is glycerol in a concentration of about 40%.

5. The method recited in claim 2 wherein said humectant sorbitol in a concentration of about 30%.

6. The method recited in claim 3, in which said antifungal formulation is introduced in the oral cavity for treatment of denture stomatitis, said method further comprising:

forming a replica of the denture surface using a suitable growth medium to determine the location or severity of the Candida infection; and contacting the infected denture surface with said antifungal formulation.

7. The method recited in claim 6 wherein said humectant comprises sorbitol in a concentration from about 20% to about 50%.

8. The method recited in claim 6 wherein said humectant is glycerol in a concentration of about 40%.

9. The method recited in claim 7 wherein said humectant is sorbitol in a concentration of about 30%.

10. The method recited in claim 6 wherein said antifungal formulation further includes carriers sweetening, coloring, and/or flavoring agents.

11. A kit for the detection and treatment of denture stomatitis and Candida infections of a surface or cavity of a denture or oral cavity, in a container which comprises:

(a) antifungal formulation consisting essentially of a humectant in a concentration of from about 20% to about 80%, and lytic activating agents selected from the group consisting of inorganic monovalent anions in a concentration of 0.5% to 2% said inorganic monovalent anions of bicarbonate, thiocyanate, chloride and fluoride ions; anionic surfactant detergent in a concentration from 0.05% to about 1%, said anionic surfactant detergent is selected from the group consisting of sodium lauroyl sarcosinate and sodium lauroyl sulfate; and non-ionic surfactant detergent in a concentration of from about 0.01% to about 3%, said non-ionic surfactant detergent is selected from the group consisting of Tween 20, polymers of polyoxyethylene and polymer of polypropylene, (b) a growth medium for contacting the denture and palatal surface of the oral cavity to be treated.

12. The kit recited in claim 11, wherein said growth medium includes a fungal growth medium.

13. The kit recited in claim 12, further including a wax for surrounding the periphery of the denture surface prior to contacting with the said fungal growth medium.

14. A method as recited in claim 1, wherein said Candida infection treated is caused by the species *Candida albicans.*

15. A method as recited in claim 1, wherein said surface or cavity is the surface or cavity of a denture or the oral cavity, which is infected with Candida in a bacterial plaque matrix.

16. A method as recited in claim 6, wherein said Candida infection treated is caused by the species *Candida albicans*.

17. A method as recited in claim 6, wherein said surface or cavity is the surface or cavity of a denture or the oral cavity, which is infected with Candida in a bacterial plaque matrix.

18. A kit as recited in claim 12, wherein said fungal growth medium is a Candida specific growth medium.

19. A kit as recited in claim 12, wherein said fungal growth medium is a *Candida albicans* specific fungal growth medium.

* * * * *

UNITED STATES PATENT AND TRADEMARK OFFICE
CERTIFICATE OF CORRECTION

PATENT NO. : 5,270,032

DATED : December 14, 1993

INVENTOR(S) : Jerry P. Pollock, Robert Renner and Ralph P. Santarpia, III

It is certified that error appears in the above-identified patent and that said Letters Patent is hereby corrected as shown below:

IN THE DRAWINGS:

In Fig. 1, Legend, now reads "(Lauroyl) Sulfate", should read --(Lauryl) Sulfate--.

In Column 1, Line 11, now reads "October 4, 1990 now abandoned.", should read -- October 4, 1990 issued as U.S. Patent No. 5,185,153 on February 9, 1993.--;

In Column 1, Line 25, now read "albicans", should read -- C. albicans --.

In Column 3, Line 47, now reads "ar", should read -- are--;

In Column 4, Line 12 and Line 13, now reads the range 30% to 80% should read --30% to 50%--;

UNITED STATES PATENT AND TRADEMARK OFFICE
CERTIFICATE OF CORRECTION

PATENT NO. : 5,270,032

DATED : December 14, 1993

INVENTOR(S) : Jerry P. Pollock, Robert Renner and Ralph P. Santarpia, III

It is certified that error appears in the above-identified patent and that said Letters Patent is hereby corrected as shown below:

| | | |
|---|---|---|
| In Column 5, Line 47, | | now reads the range "30" to 80%", should read --30% to 50%--; |
| In Column 7, Line 2, | | now reads "removing=denture", should read --removing a denture--; |
| In Column 8, Line 4, | | the phrase "sodium lauroyl sulfate", should read --sodium lauryl sulfate--; |
| | Line 5, | now reads "sodium lauryl sarcosinate", should read --sodium lauroyl sarcosinate--; |
| | Line 30, | now reads "sodium lauryl sarcosinate", should read --sodium lauroyl sarcosinate--; |
| | Line 32, | the phrase "sodium lauroyl sulfate", should read --sodium lauryl sulfate--; |

UNITED STATES PATENT AND TRADEMARK OFFICE
CERTIFICATE OF CORRECTION

PATENT NO. : 5,270,032

DATED : December 14, 1993

Page 3 of 4

INVENTOR(S) : Jerry P. Pollock, Robert Renner and Ralph P. Santarpia, III

It is certified that error appears in the above-identified patent and that said Letters Patent is hereby corrected as shown below:

| | |
|---|---|
| In Column 9, Line 36, | now reads "(data now shown)", should read --(data not shown)--; |
| Line 39 and Line 40, | now reads "sodium lauryl sarcosinate", should read --sodium lauroyl sarcosinate--; |
| Line 42, | now reads "sodium laurylsarcosinate", should read --sodium lauroyl sarcosinate--; |
| Line 43 and Line 44, | now reads "sodium lauryl sarcosinate", should read --sodium lauroyl sarcosinate--. |
| In Column 13, Line 32, | now reads "time", should read --times--; |
| In Column 15, Line 18, | now reads "weeks.", should read --weeks)--; |
| After Table 15, | insert the phrase --apply about 200 ml. daily to vaginal mucosal surfaces--. |

UNITED STATES PATENT AND TRADEMARK OFFICE
CERTIFICATE OF CORRECTION

PATENT NO. : 5,270,032
DATED : December 14, 1993
INVENTOR(S) : Jerry P. Pollock, robert Renner and Ralph P. Santarpia, III It is certified that error appears in the above-identified patent and that said Letters Patent is hereby corrected as shown below:

IN THE CLAIMS:

In Claim 1, Column 15,
    Line 56     now reads "movement anions", should read --monovalent anions--;

Line 63 and 64,     now reads "sodium lauroyl sulfate;", should read --sodium lauryl sulfate--.

In Claim 11, Column 16,
    Line 47 and Line 48,     now reads "sodium lauroyl sulfate", should read --"sodium lauryl sulfate"--.

Signed and Sealed this

Sixth Day of June, 1995

BRUCE LEHMAN

*Attest:*

*Attesting Officer*     *Commissioner of Patents and Trademarks*